(12) United States Patent
Chiu

(10) Patent No.: US 7,581,262 B2
(45) Date of Patent: Sep. 1, 2009

(54) PANTIES WITH SKIN-WHITENING EFFECT

(76) Inventor: Chien-Jung Chiu, 6F.-1, No. 124, Min-an W. Rd., Xinzhuang City (TW) 241

( * ) Notice: Subject to any disclaimer, the term of this patent is extended or adjusted under 35 U.S.C. 154(b) by 0 days.

(21) Appl. No.: 12/149,700

(22) Filed: May 7, 2008

(65) Prior Publication Data
US 2009/0077719 A1   Mar. 26, 2009

(30) Foreign Application Priority Data
Sep. 21, 2007   (TW)   .............................. 96215870 U

(51) Int. Cl.
*A41B 9/00*   (2006.01)
(52) U.S. Cl. .............................. 2/400; 2/406; 424/401; 424/402
(58) Field of Classification Search ............. 2/400–408; 604/385.01–397, 364, 358; 424/401, 402
See application file for complete search history.

(56) References Cited

U.S. PATENT DOCUMENTS

| 5,232,769 | A | * | 8/1993 | Yamato et al. | ............... | 442/123 |
| 5,416,929 | A | * | 5/1995 | Braunstein | ..................... | 2/406 |
| 6,570,054 | B1 | * | 5/2003 | Gatto et al. | ................. | 604/364 |
| 6,793,930 | B2 | * | 9/2004 | Gatto et al. | ................. | 424/401 |
| 6,897,348 | B2 | * | 5/2005 | Malik | .......................... | 602/48 |

* cited by examiner

*Primary Examiner*—Gloria Hale

(57) ABSTRACT

A pair of panties with a skin-whitening effect comprises a wearing space defined therein, and one or more gel blocks each covered by a release film attached to the panties so as to press close to a groin, a waist, and borders between hips and legs of a user to wear the panties. Thereby, after the release film is torn and the panties are worn by the user, skin-whitening, skin-color-lighting, and wrinkle-softening agents contained in the gel blocks can perform skin-whitening, skin-color-lighting, and wrinkle-softening treatment on the above-mentioned user's body portions, while not disturbing the user's daily life.

6 Claims, 6 Drawing Sheets

PANTIES WITH SKIN-WHITENING EFFECT

BACKGROUND OF THE INVENTION

1. Technical Field

The present invention relates to panties and, more particularly, to a pair of panties with skin-whitening and hip-lifting effects.

2. Description of Related Art

It is said that the love of beauty is an essential part of all healthy human nature. Therefore we can see numerous skin-whitening products and skin care products providing skin care and skin-whitening effects for conspicuous portions of human bodies, such as face, facial features, limbs, etc. on the market. Thus, various options of skin care and skin-whitening products aimed at the above-mentioned human body portions are commercially available, and information about taking care of the above-mentioned human body portions is easily accessible.

However, in addition to the aforementioned conspicuous body portions, inconspicuous body portions, such as groin and borders between hips and legs, can also gradually get dark due to friction between skin and skin or between skin and clothes, dirt accumulation, melanin deposition and so on.

Therefore, some skin-whitening products, which are aimed at whitening the darkened portions such as the groin and borders between hips and legs, have been introduced. These products, either in the form of ointment or skin patches, are to be applied to a user's groin and borders between hips and legs and after the application of the skin-whitening products, the user usually has to stay still for a period of time long enough for the products to be absorbed, resulting in inconvenience of the application of the products.

Moreover, as described above, the friction between skin and skin or between skin and clothes at the groin and borders between hips and legs is unavoidable. Though skin-whitening products are commercially available for caring and whitening the groin, waist, and borders between hips and legs at night and during the user's sleep, in day time or when the user leaves home, such caring and whitening treatment have to be broken off, thereby adversely affecting the caring and whitening effects.

Hence, how to remedy the problems and defects of the prior art products is an issue for manufacturers in the art and the inventor of the present invention to work out.

SUMMARY OF THE INVENTION

In view of the defects of the conventional products, after extensively collecting information, comprehensively evaluating and considering, and, trials and modifications based on years experience, the inventor of the present invention herein proposes a pair of panties with a skin-whitening effect.

A primarily objective of the present invention is to provide a pair of panties having a skin-whitening effect, wherein a wearing space defined inside the panties has attached thereto one or more gel blocks, so that the blocks can press close to a groin, a waist, borders between hips and legs or pudendum of a user to wear the panties without the problem of the conventional products about disturbing a user's walking when being applied to a user's groin, waist, borders between hips and legs or pudendum so that when the panties of the present invention are worn by the user, skin-whitening, skin-color-lighting, and wrinkle-softening agents contained in the gel block can perform skin-whitening, skin-color-lighting, and wrinkle-softening on the above-mentioned user's body portions, while not disturbing the user's daily life.

A secondary objective of the present invention is to provide a pair of panties having a front wrapping portion, a back wrapping portion extended backward from the front wrapping portion, and an upper wrapping portion extended upward from the front wrapping portion and the back wrapping portion, wherein the upper wrapping portion is made of an elastic fabric, and the back wrapping portion has a plurality of flexible portions so that the elastic upper wrapping portion serves to shape the user's waist, and the flexible portions serve to lift the user's hips.

BRIEF DESCRIPTION OF THE DRAWINGS

The invention as well as a preferred mode of use, further objectives and advantages thereof, will best be understood by reference to the following detailed description of an illustrative embodiment when read in conjunction with the accompanying drawings, wherein.

DETAILED DESCRIPTION OF THE PREFERRED EMBODIMENT

Figure 1:
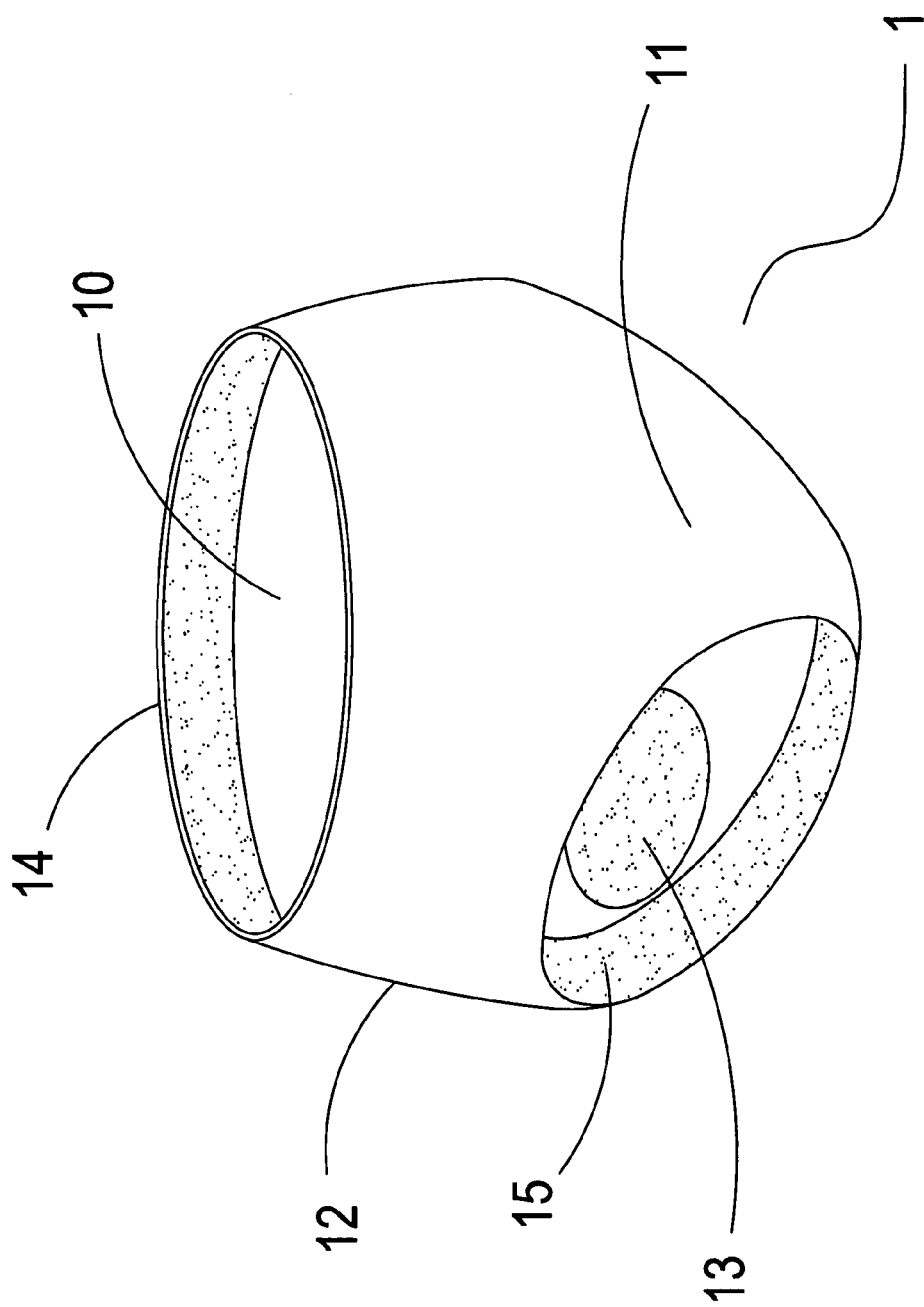
FIG. 1 is an external perspective view of an embodiment according to the present invention.
Figure 2:
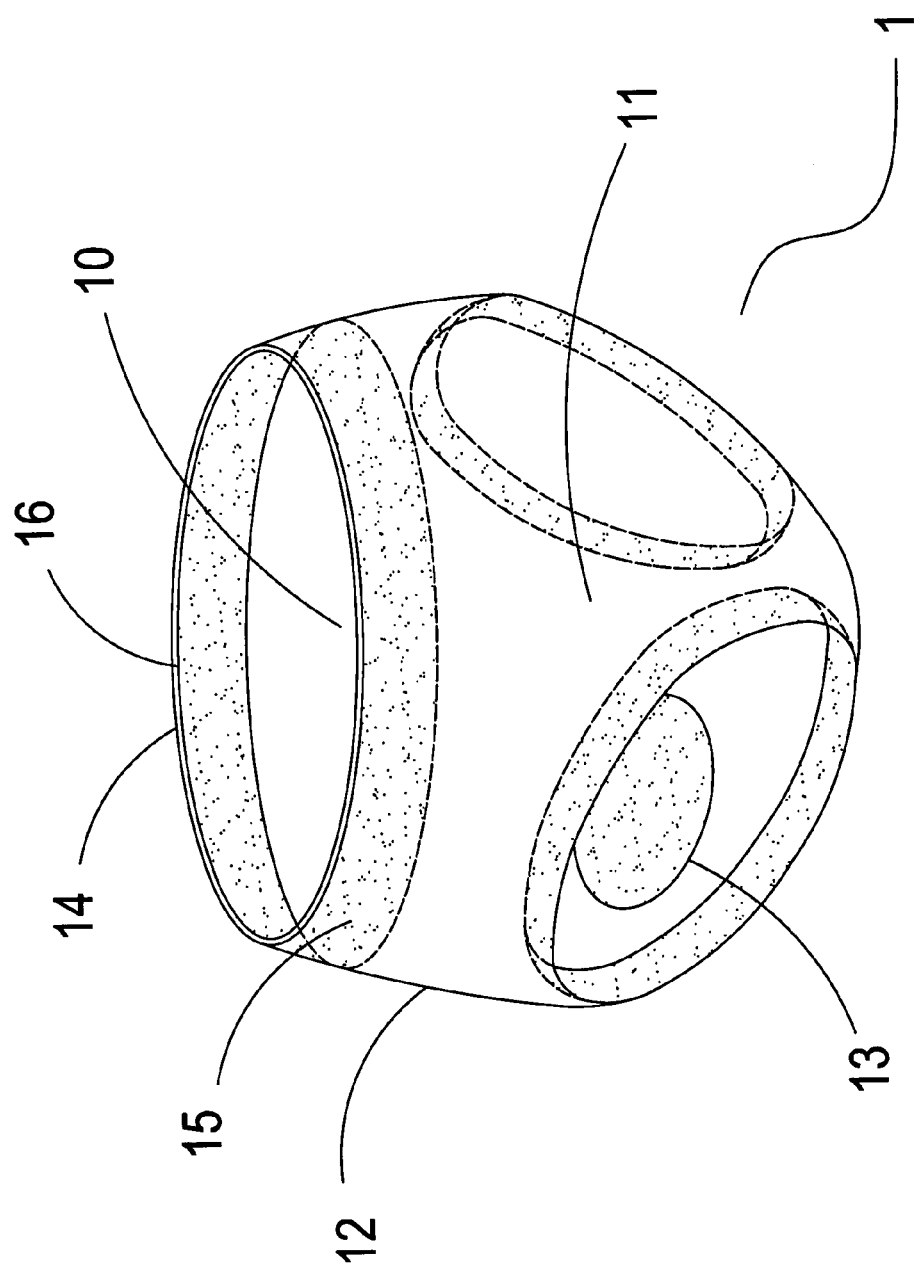
FIG. 2 is an internal perspective view of the embodiment according to the present invention.
Figure 3:
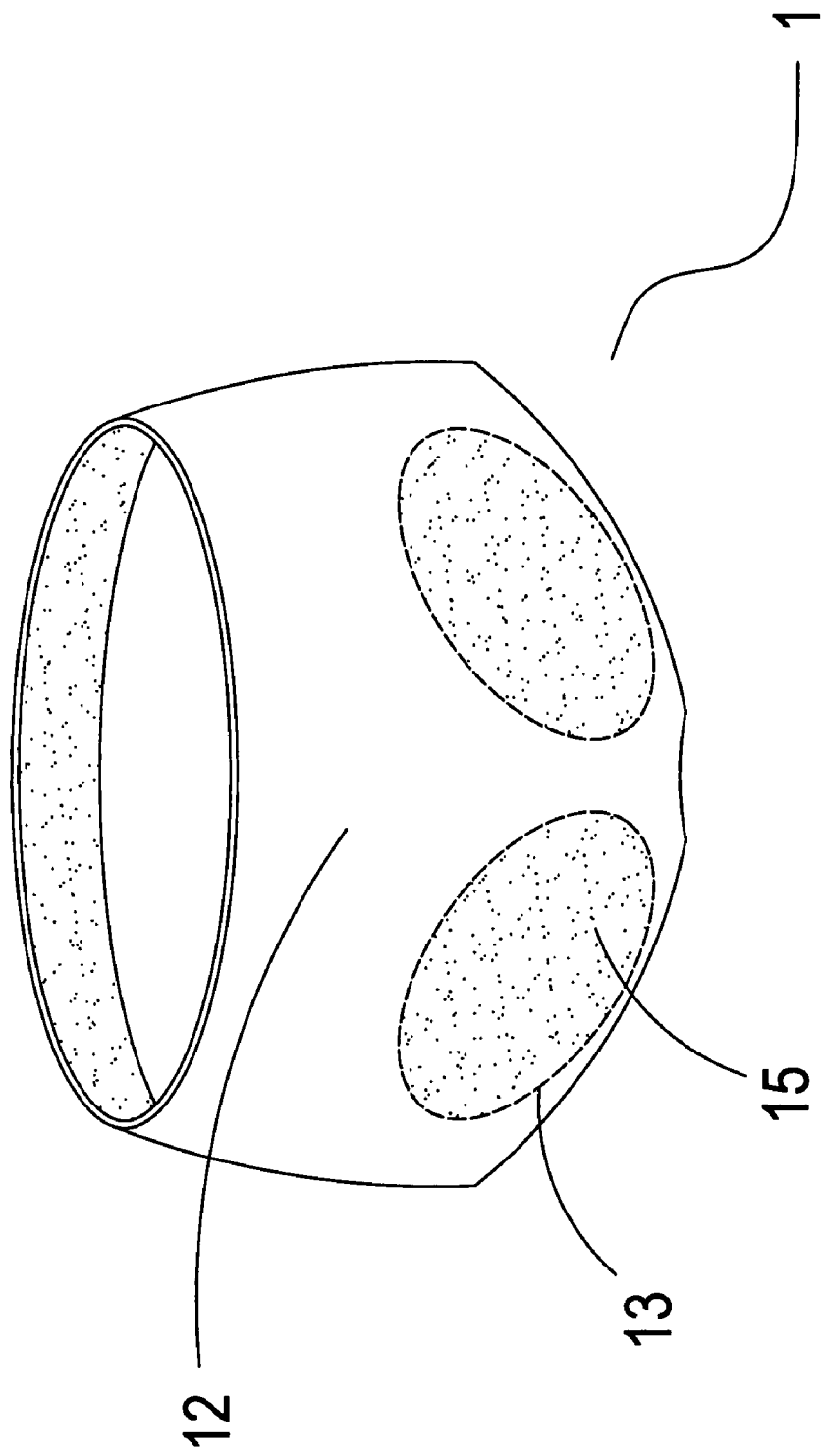
FIG. 3 is a partially sectional view of the embodiment according to the present invention.
Figure 4:
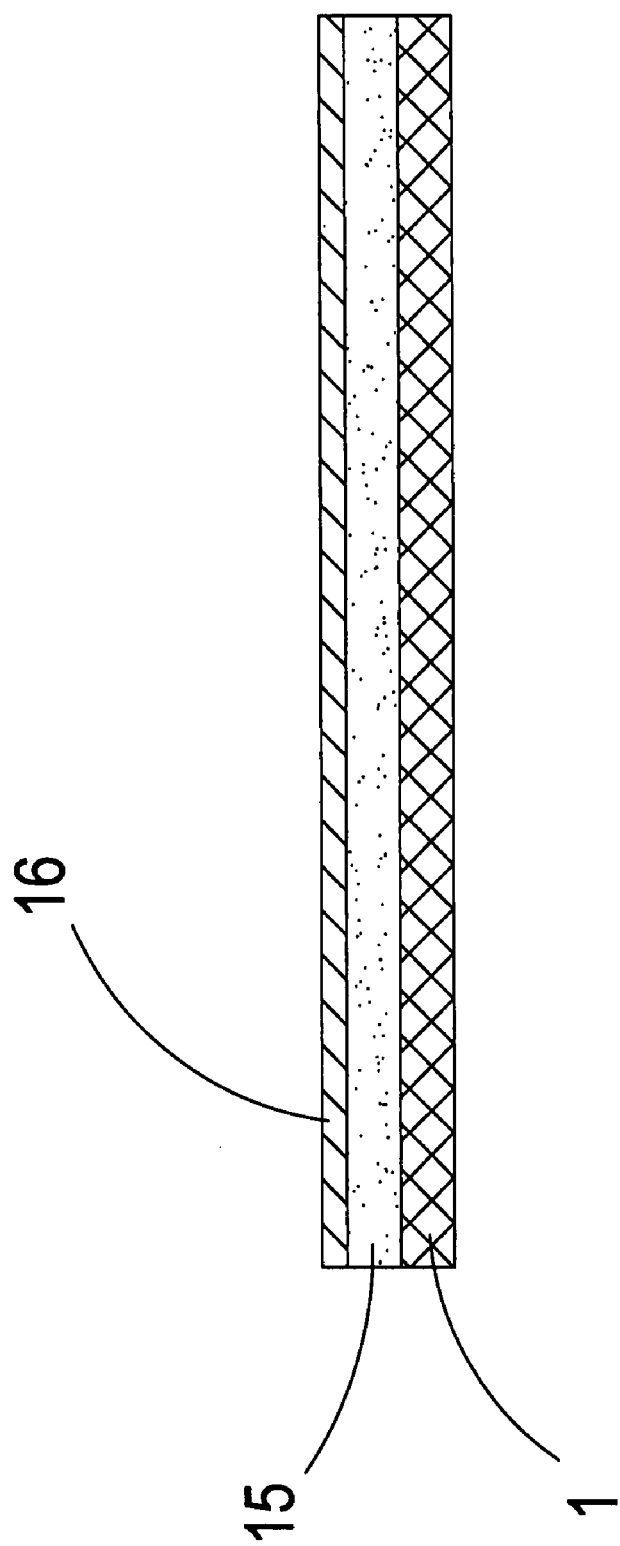
FIG. 4 is another partially sectional view of the embodiment according to the present invention.

For best illustrating the technical means and structures adopted in the present invention in order to achieve the above objectives, one preferred embodiment of the present invention is provided and the features and effects thereof will be described in detail hereafter.

Please refer to FIGS. 1, 2, 3 and 4 for an external perspective view, an internal perspective view, and a first and second partially sectional views. According to the drawings, a pair of panties 1 comprises a front wrapping portion 11, a back wrapping portion 12 extended backward from the front wrapping portion 11 and having a plurality of flexible portions 13, an upper wrapping portion 14 extended upward from the front wrapping portion 11 and the back wrapping portion 12, and is made of an elastic fabric. A wearing space 10 is thereby defined amid the upper wrapping portion 14, back wrapping portion 12 and front wrapping portion 11 and in communication with the outside.

Furthermore, the panties 1 have attached thereto one or more gel blocks 15, which may be attached to an inner surface of any of the upper wrapping portion 14, back wrapping portion 12 and front wrapping portion 11 facing the wearing space 10. Each said gel block 15 has a release film 16 provided thereon. In addition, the panties 1 may be made of a non-woven fabric or a silk fabric while the gel block 15 may contain any one of Arbutin, Kojic acid, L-Ascorbic Acid, collagen, Ubiquinol, and Hydroquinone.

In use of the disclosed subject matter, a user can tear the release film 16 and put on the panties 1, so that the skin-whitening, skin-color-lighting, and wrinkle-softening agents contained in the gel blocks 15 can perform skin-whitening, skin-color-lighting, and wrinkle-softening treatment on the user's body portions, while not disturbing the user's daily life.

Figure 5:
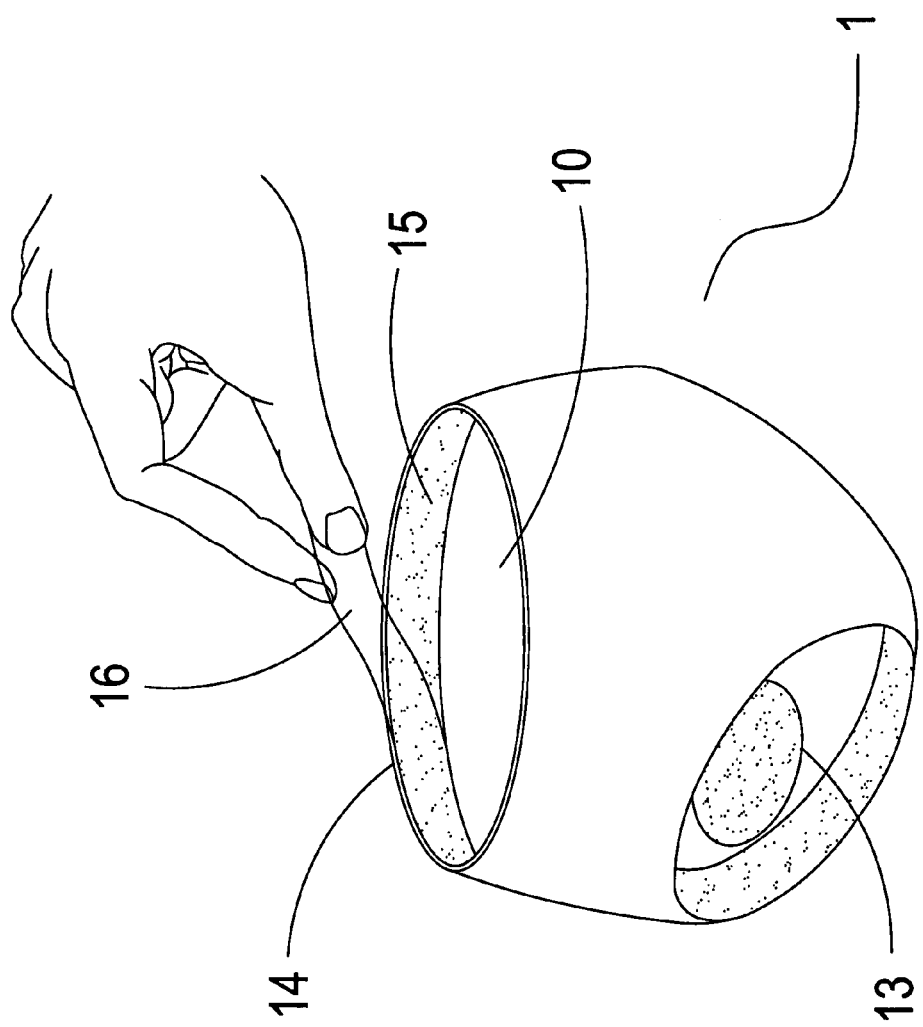
FIG. 5 is an applied view of the embodiment according to the present invention.
Figure 6:
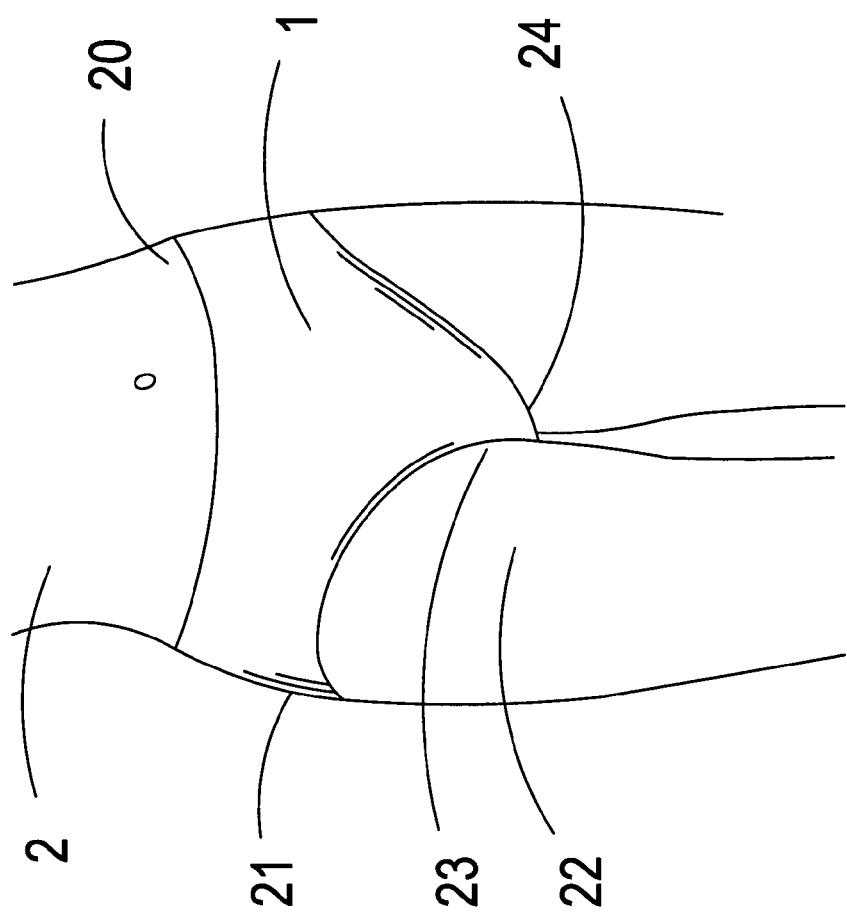
FIG. 6 is another applied view of the embodiment according to the present invention.

Please also refer to FIGS. 5 and 6, which are the first and second applied views of the embodiment of the present invention. According to the drawings, applications of the aforementioned structural and assembling design of the present invention will be further illustrated below.

The plural gel blocks 15 are arranged at portions of the inner surface of the panties 1 corresponding to a waist 20, borders between hips 21 and legs 22, a groin 23 and a pudendum 24 of a human body 2, and covered by a released film 16, respectively. In use, the user tears the release film to make the gel blocks 15 in communication with the wearing space 10 so that when the user puts on the panties 1, the gel blocks 15 can contact the waist 20, borders between hips 21 and legs 22, groin 23 and pudendum 24 of the human body 2 and the skin-whitening, skin-color-lighting, and wrinkle-softening agents contained in the gel block 15 can be absorbed by the user's skin so as to achieve skin-whitening, skin-color-lighting, and wrinkle-softening effects. During the skin-whitening, skin-color-lighting, and wrinkle-softening process, the user is not required to lie or sit still, but is allowed to continue any activity the user is performing such as working, shopping, meeting, house keeping, etc, so that the user can receive skin-whitening, skin-color-lighting, and wrinkle-softening treatment any time.

In addition, when the panties 1 are worn, not only the upper wrapping portion 14 can shape the user's waist 20 by tightening the waist 20 because the upper wrapping portion 14 is made of the elastic fabric, but also the flexible portions 13 can lift the user's hips so as to improve limp hips 21 and achieve effects of tightening and lifting the hips 21.

Although the particular embodiment of the invention has been described in detail for purposes of illustration, it will be understood by one of ordinary skill in the art that numerous variations will be possible to the disclosed embodiments without going outside the scope of the invention as disclosed in the claims.

What is claimed is:

1. A pair of panties with a skin-whitening effect, comprising:
   the pair of panties having a front wrapping portion, a back wrapping portion extended from the front wrapping portion, and a wearing space defined between the front wrapping portion and the back wrapping portion;
   one or more gel blocks containing skin-whitening agent, attached to an inner surface of the panties and facing the wearing space; and one or more release films, each covering a respective said gel block.

2. The panties of claim 1, wherein the panties are made of any one of a non-woven fabric and a silk fabric.

3. The panties of claim 1, wherein the gel blocks are attached to the inner surface of the panties at the front wrapping portion and the back wrapping portion corresponding in position to a groin, a waist, a pudendum and lower hips of a user to wear the panties.

4. The panties of claim 1, wherein an upper wrapping portion is extended upward from the back wrapping portion and a front wrapping portion and is made of an elastic fabric.

5. The panties of claim 1, wherein the gel block functions as a carrier for carrying chemical skin care and skin-whitening agents.

6. The panties of claim 4, wherein the upper wrapping portion has attached thereto one or more gel blocks in which each said gel block is covered by a release film.

* * * * *